| United States Patent [19]
Purohit et al.

[11] Patent Number: 4,966,754
[45] Date of Patent: Oct. 30, 1990

[54] PRESERVATION OF COSMETIC COMPOSITIONS

[75] Inventors: Prakash C. Purohit; Lal G. Ramdeen, Minneapolis, Minn.

[73] Assignee: Aveda Corporation, Minneapolis, Minn.

[21] Appl. No.: 229,234

[22] Filed: Aug. 8, 1988

[51] Int. Cl.$^5$ .................. A61K 35/78; A61K 7/06
[52] U.S. Cl. .................. 424/195.1; 514/844; 514/845; 514/846; 514/847
[58] Field of Search .................. 424/195.1; 514/844, 514/845, 846, 847

[56] References Cited

U.S. PATENT DOCUMENTS 4,784,849  11/1988  Tutsky .................. 514/847 X

FOREIGN PATENT DOCUMENTS 88412  5/1984  Japan .................. 424/195.1
32705  2/1985  Japan .................. 424/195.1

OTHER PUBLICATIONS

*Kirk–Othmer Encyclopedia of Chemical Technology,* First Edition, vol. 9, pp. 569–591 (1952).
Balsam, *Cosmetics Science and Technology,* Second Edition, vol. 2, pp. 599–633 (1972).
Pianotti, *Chem. Abs.,* 108, 81855f (1988).
Ogilets et al., *Chem. Abs.,* 107, 242442r (1987).
Lust, *The Herb Book,* pp. 143–144, 155, 160, 260–261, 327–329, 398–399, 543–544 (1974).
Hawley, *The Condensed Chemical Dictionary,* Tenth Edition, pp. 50, 409, 502, 611, 838, 959–960 (1981).

*Primary Examiner*—John W. Rollins
*Assistant Examiner*—W. Catchpole

[57] ABSTRACT

A cosmetic composition containing a dermatologically acceptable carrier or vehicle and certain essential oils as a preservative. The essential oil provides antimicrobial assurance against *Apergillus niger, Candida albicans, Staphylococcus aureus* and *Pseudomonas aeruginosa.* A method of preparing the preserved cosmetic composition is also described.

2 Claims, No Drawings

PRESERVATION OF COSMETIC COMPOSITIONS

BACKGROUND OF THE INVENTION

1. Field of the Invention

This invention relates to the preservation of cosmetic compositions, which contain a dermatologically acceptable carrier or vehicle, against four microorganisms, namely *Aspergillus niger, Candida albicans, staphyloccus aureus* and *Pseudomonas aeruginosa*. The invention relates to the cosmetic compositions containing the preservative and a method and composition for incorporating the preservative into the cosmetic composition.

2. Description of Related Art

For years research has been conducted in efforts to produce a cosmetic preparation that also possesses microbiocidal properties, an antimicrobial cosmetic composition. Thus, cosmetics have been formulated with a variety of bactericides which are effective against microorganisms such as *Staphylococcus aureus*. Such bactericides or antimicrobial compounds are generally synthetic or compounds such as methyl or propyl paraben, Dowicil 200, or various quaternary compounds. Care must be taken that the antimicrobial agents are non toxic and do not irritate the skin to which the cosmetic is applied. Not only must the cosmetic vehicle or carrier be dermatologically acceptable, but also the antimicrobial agent, or preservative agent, should be dermatologically acceptable. An acceptable cosmetic should be preserved against, or contain an antimicrobial agent effective against, at least four groups of microorganisms, 1. Molds (*Aspergillus niger*), 2. Yeasts (*Candida albicans*), 3. Gram positives (*Staphylococcus aureus*) and 4. Gram negatives (*Pseudomonas aeruginosa*).

DESCRIPTION OF THE INVENTION

It has now been determined that certain of the essential oils are effective as antimicrobial agents against the four microorganisms, *Aspergillus niger, Candida albicans, Staphylococcus aureus* and *Pseudomonas aeruginosa*. There are hundreds of natural essential oils available. A good discussion of essential oils, their composition and production, can be found in Kirk-Othmer Encyclopedia of Chemical Technology, Third Edition, Volume 16, pages 307-329, copyright 1981, John Wiley & Sons, Inc., the disclosure of which is herein incorporated by reference. Applicants have found forty-two oils and their isomers which are useful against all four microorganisms and are accordingly effective for use as preservatives in cosmetic applications. The oils are useful alone, but a mixture of these provide the most effective preservative, or antimicrobial action The oils, by the emulsified composition of this invention, and the method of incorporation described herein, are easily and readily capable of incorporation into cosmetic compositions of virtually any cosmetic vehicle or carrier. Thus, the antimicrobial compositions of this invention are comprised of a dermatologically acceptable vehicle or carrier and as a preservative or antimicrobial agent, an effective amount of one or more of the forty-two essential oils, found to be effective against all four microorganisms noted above. These oils, hereinafter specified, are safe, mild and effective preservative agents compatible with conventional, known cosmetic ingredients.

Because of the nature of the essential oils, they cannot merely be added to the cosmetic vehicle or composition. A means of incorporating the oils into the cosmetic composition has been discovered, however. To incorporate the oils, an emulsion or solution thereof is first formed in a solubilizer or dispersant agent such as a polyoxyethylene sorbitan ester. Such materials are available commercially under the "POLYSORBATE" name, i.e. Polysorbate 20 or Polysorbate 80. Although perhaps not necessary to explain, Polysorbate 80 is described as a polyoxyethylene sorbitan mono-oleate, sometimes also described as sorbitan monooleatepolyoxyethylene. The compound is accordingly an oleate ester of sorbitol and its anhydrides condensed with polymers of ethylene oxide having approximately 20 oxyethylene units. The common fatty acid esters are the oleate noted above, laurate and stearate. The dispersant may be generally described as a polyoxyethylene sorbitan fatty acid ester in which the fatty acid contains 8 to 22 carbon atoms, more commonly 12-18 carbon atoms, and preferably 18 carbon atoms and the number of oxyethylene units will vary between 5-40, preferably on the order of 10 to 30 with about 20 being most preferred.

In the emulsion or solution of the sorbitan ester and the essential oil, the ratio by weight of ester to oil will vary from about 2:1 to about 6:1 with about 3:1 being preferred. Thus the antimicrobial oil will comprise from about 15% to about 35% by weight based on the total weight of oil and solubilizer. The emulsion is prepared by mixing the sorbitan ester and the oil under vigorous conditions as in a vortex mixer.

Many cosmetic preparations are emulsions of a water phase and an oil phase. In preparing such compositions the water phase and oil phase components are separately prepared and the two phases mixed at an elevated temperature generally above 40° C. to about 60°-90° C., preferably about 75° C., until a uniform mixture is achieved. The mixture is then cooled to a temperature of about 40° C. at which time the premix blend of sorbitan ester and essential oils is added slowly with mixing until a uniform cosmetic composition results. The temperatures will vary somewhat dependent on the particular cosmetic composition being prepared. In addition to emulsion types (oil-in-water or water-in-oil) the cosmetic composition may also consist of a single aqueous or aqueous-alcoholic phase.

By "cosmetic" as the term is used herein is intended to include all types of products which are applied in any manner directly to a person for cleansing or embellishment purposes. Such "cosmetic" compositions accordingly require a dermatologically acceptable carrier or vehicle.

Included within the scope of the term "cosmetic" are creams and lotions, such as cleansing creams, facial creams, shaving creams, hand lotions and balms, antiperspirant lotions and creams, cleansing gels, bath oils and gelees, hair dressing gels, and creams and conditioners, make-up, suntan oils, lotions and creams and other cosmetic applications.

The essential oils and their isomers which have been discovered to posses antimicrobial properties against all four of the micro-organisms earlier noted are:

1. Armoise
2. Basil
3. Bay
4. Bois de Rose
5. Caraway
6. Cardamon
7. Cedarwood
8. Cinnamon Bark -continued 9. Coriander
10. Clovebud
11. Estragon
12. Fennel Sweet
13. Geraniol from Palmarosa oil
14. Juniper Berries
15. Lemongrass 80% rectified
16. Linalool ex Bois de Rose
17. Marjoram
18. Methol Crystals laevo
19. Neroli Bigarde Petals
20. Oakmoss Empuree
21. Otto Rose Bulgarian
22. Rosemary
23. Thyme
24. Vanilla Resinold
25. Wintergreen
26. Eugenol
27. Linalyl Formate
28. Oil of Clove (Indonesian)
29. Oil of Pimento Berry (W. Indian)
30. Oil Bay (W. Indian Redist.)
31. Natural Bitter Almond Oil
32. Wine Fusel Oil American
33. Oil Pennyroyal Spanish
34. Oil Litsea Cubeba
35. Oil Lovage
36. Oil Buchu Leaves
37. Laevo Linalool
38. Hydroxycitronella ex Citradora
39. Hyperabsolute Styrax Incolore
40. Hydroxycitronella ex Citronella
41. Iso Eugenol
42. Terpeneol Super While each of the above has been found to be effective, preferably a mixture of these has been found to be the most effective at the levels generally employed in a cosmetic application such as a lotion or cream. The blend of sorbitan ester and oil is preferably added or incorporated into the cosmetic composition at a level of about 8% or more by weight of the total cosmetic composition. At the preferred 3:1 weight ratio of sorbitan ester and oil, the anitmicrobial essential oil will be present at a level of about 2% by weight of the total cosmetic composition. Higher amounts of essential oil above 2% will also be effective. However, it is generally not necessary to exceed 3 or 5% thereof depending largely on the fragrance desired. A preferred blend of oils which provides optimum antimicrobial properties, providing a clean kill within 72 hours of all four microorganisms noted earlier hereinabove, is as follows:

| Blend X | |
|---|---|
| Percent by Weight | Essential Oil |
| 20.00 | Linalool (ex. Bois de Rose) |
| 5.00 | Geraniol (ex. Palmarosa) |
| 5.00 | Lemongrass 80% rectified |
| 20.00 | Bois de Rose |
| 20.00 | Cedarwood Oil |
| 5.00 | Marjoram Oil |
| 2.00 | Cinnamon Bark Oil |
| 2.00 | Cardamon Oil |
| 3.00 | Neroli Bigarde Petals Oil |
| 2.00 | Vanilla Resinoid |
| 5.00 | Coriander Oil |
| 2.00 | Oakmoss empuree |
| 2.00 | Armoise Oil |
| 5.00 | Menthol Crystals laevo |

-continued

| Blend X | |
|---|---|
| Percent by Weight | Essential Oil |
| 2.00 | Rose absolute concrete (wax) |

EXAMPLE 1

In use in cosmetic preparations or compositions it is generally necessary that the oils be diluted in order to incorporate them easily into the cosmetic composition. It was found that conventional disc methods were not satisfactory for testing for antimicrobial properties of the essential oils. Accordingly, a new method of identifying the essential oils for antimicrobial activity was developed which utilizes the novel blend of sorbitan ester and essential oil. This test which follows below is the one employed in evaluating an identifying the antimicrobial activity of the forty-two oils specified hereinabove.

ANTIMICROBIAL TEST

A mixture of 3 parts Polysorbate 20 and 1 part essential oil is prepared by mixing well in a Vortex shaker. A mixture of 0.2, 0.4 and 0.8 grams of this blend (equal to 0.5%, 1.0% and 2.0% respectively essential oil) is added to 10 milliliters of sterile nutrient broth in a test tube and vigorously vortexed. A liquid, 24-hour culture of each of the four microorganisms is introduced into separate test tubes containing the essential oil blend with sorbitan ester and the nutrient broth. One drop of liquid culture contained about 1 million microorganisms. The test tubes are vigorously shaken and incubated for 72 hours at 37° C. Growth of microorganisms is examined by a streak of the foregoing preparation on Trypticase soy agar (TSA) plates. Growth on the TSA plate indicated no inhibition and thus no antimicrobial action in the blend. No growth on the plate indicated inhibition and antimicrobial activity.

Using the preferred blend of essential oils, Blend X described earlier above, the results of the test above at the 0.5%, 1.0% and 2.0% levels of essential oil was observed, with the following results:

TABLE I

| Level | a<br>A. niger | b<br>C. albicans | c<br>S. aureus | d<br>Ps. aeruginosa |
|---|---|---|---|---|
| 0.5% | No growth | No growth | No growth | Growth |
| 1.0% | No growth | No growth | No growth | Growth |
| 2.0% | No growth | No growth | No growth | No growth |

The results in Table I show a clean kill of all four microorganisms in 72 hours at the 2% level of essential oil.

EXAMPLE 2

In order to test the effectiveness of the essential oil, Blend X described earlier, in a conventional cosmetic composition or cleansing cream was prepared using the formulation and procedure below:

Formulation

| Formulation | |
|---|---|
| Percentage by weight | |

| | -continued |
|---|---|
| | Water Phase |
| 42.44 | Deionized Water |
| 1.0 | Guar hydroxypropyltrimonium chloride |
| 2.0 | Glycerin USP 96% |
| 0.5 | Potassium Stearate |
| 3.5 | Sodium lauriminodipropionate |
| 0.5 | Allantoin |
| 3.33 | Sodium Cocoyl Isethionate |
| | Oil Phase |
| 3.0 | Glyceryl Stearate |
| 25.0 | Caprylic/capric triglyceride |
| 3.75 | Stearic Acid |
| 4.5 | Cetyl Alcohol |
| 1.12 | PEG 5 soya sterol |
| 0.38 | Soy Sterol |
| 1.5 | Jojoba Oil |
| 0.38 | Tocopherol |
| | Antimicrobial Premix |
| 2.0 | Essential Oil (Blend X) |
| 6.0 | Polysorbate 20 |

Procedure

The guar gum is hydrated in water and then the remaining ingredients of the water phase are added in sequential order with constant mixing. The phase is heated to 75° C. In a separate kettle all the ingredients of the oil phase are added in sequential order and heated to 75° C. with constant mixing. The oil phase is added to the water phase and mixed while maintaining the temperature at 75° C. The mixing is continued until uniform. The cream is cooled to 40° C., and the premix blend of polysorbate 20 and Blend X is added to the cream slowly and mixed until completely uniform.

EXAMPLE 3

To test the cleansing cream of Example 2 having incorporated therein 2% of the essential oil, Blend X, 20 grams of cleansing cream was put in four 15×150 mm test tubes. Approximately one million microorganisms of each of the four types were introduced into each tube. One gram of the inoculated product was diluted with 9 milliliters of sterile diluent, plated and counts were observed. In five days counts were reduced from $1 \times 10^6$ to zero.

TABLE II

| Time (hrs) | Count |
|---|---|
| 0 | $1 \times 10^6$ |

TABLE II-continued

| Time (hrs) | Count |
|---|---|
| 48 | $8 \times 10^2$ |
| 120 | 0 |

The foregoing illustrates that Blend X is an effective preservative in a cosmetic.

Similar results are obtained with other cosmetic applications and compositions such as lotions, creams other than cleansing creams, single or multiple phase systems, solutions or emulsions.

What is claimed:

1. A method of preserving a cosmetic composition from microbial action of the microorganisms *Aspergillus niger, Candida albicans, Staphylococcus aureus* and *Pseudomonas aeruginosa* comprising incorporating into said cosmetic composition an essential oil having antimicrobial activity against all four of said microorganisms, wherein said antimicrobial essential oil is a mixture of essential oils having the following composition by weight:

| Percentage By Weight | Essential Oil |
|---|---|
| 20.00 | Linalool ex Bois de Rose |
| 5.00 | Geraniol ex Palmarosa |
| 5.00 | Lemongrass 80% rectified |
| 20.00 | Bois de Rose |
| 20.00 | Cedarwood Oil |
| 5.00 | Marjoram Oil |
| 2.00 | Cinnamon Bark Oil |
| 2.00 | Cardamon Oil |
| 3.00 | Neroli Bigarde Petals Oil |
| 2.00 | Vanilla Resinoid |
| 5.00 | Coriander Oil |
| 2.00 | Oakmoss empuree |
| 2.00 | Armoise Oil |
| 5.00 | Menthol Crystals laevo |
| 2.00 | Rose absolute concrete wax | and wherein said antimicrobial essential oil is incorporated into said cosmetic composition by first dissolving said antimicrobial essential oil in a polyoxyethylene sorbitan ester wherein the ratio by weight of said sorbitan ester to said antimicrobial essential oil is in the range of 2:1 to 6:1 and adding said resulting sorbitan ester and essential oil mixture to said cosmetic composition in an amount to provide said antimicrobial essential oil in said cosmetic composition of at least 2% by weight of said cosmetic composition.

2. A method as defined in claim 1 wherein said composition is a cosmetic cream or lotion.

* * * * *